(12) United States Patent
Mestieri et al.

(10) Patent No.: US 10,436,936 B2
(45) Date of Patent: Oct. 8, 2019

(54) TRANSPARENT AND/OR SHINY OBJECT DETECTION WITH SPIN-MODULATED LIGHT

(71) Applicant: Datalogic IP Tech S.R.L., Calderara Di Reno, Bologna (IT)

(72) Inventors: Marco Mestieri, Cento (IT); Alberto Fabbri, Bologna (IT)

(73) Assignee: Datalogic IP Tech S.R.L., Calderara Di Reno, Bologna (IT)

(*) Notice: Subject to any disclaimer, the term of this patent is extended or adjusted under 35 U.S.C. 154(b) by 242 days.

(21) Appl. No.: 15/662,745

(22) Filed: Jul. 28, 2017

(65) Prior Publication Data

US 2018/0210111 A1   Jul. 26, 2018

Related U.S. Application Data

(60) Provisional application No. 62/368,812, filed on Jul. 29, 2016.

(51) Int. Cl.
| | |
|---|---|
| *G01V 8/14* | (2006.01) |
| *G01S 17/02* | (2006.01) |
| *G01S 17/88* | (2006.01) |
| *G01S 7/48* | (2006.01) |
| *G01S 7/499* | (2006.01) |
| *G02F 1/01* | (2006.01) |
| *G01N 21/21* | (2006.01) |

(52) U.S. Cl.
CPC ............. *G01V 8/14* (2013.01); *G01S 7/4802* (2013.01); *G01S 7/499* (2013.01); *G01S 17/026* (2013.01); *G01S 17/88* (2013.01); *G01N 21/21* (2013.01); *G02F 1/0136* (2013.01)

(58) Field of Classification Search
CPC . G01V 8/14; G01V 8/22; G01N 21/21; G01S 17/026; G01S 7/499
USPC ...................................... 250/225, 216, 214 R
See application file for complete search history.

(56) References Cited

U.S. PATENT DOCUMENTS

| | | | | |
|---|---|---|---|---|
| 4,547,067 A | * | 10/1985 | Watanabe | ............ G01N 21/9018 |
| | | | | 250/223 B |
| 6,545,329 B1 | | 4/2003 | Lannon, Jr. et al. | |
| 7,534,626 B2 | | 5/2009 | Parkin | |
| 7,978,394 B1 | | 7/2011 | Johnson et al. | |

(Continued)

FOREIGN PATENT DOCUMENTS

| | | |
|---|---|---|
| DE | 19801632 A1 | 5/1999 |
| JP | 3618841 B2 | 2/2005 |
| JP | 2011039008 A | 2/2011 |

OTHER PUBLICATIONS

Rinaldi, et al., "Ge-Based Spin-Photodiodes for Room-Temperature Integrated Detection of Photon Helicity," Adv. Matter., 2012, vol. 24, pp. 3037-3041.

(Continued)

*Primary Examiner* — Que Tan Le
(74) *Attorney, Agent, or Firm* — Dentons US LLP

(57) ABSTRACT

A system and method for retro-reflective imaging transparent and/or shiny objects may include generating a light signal having a spin polarization. A magnetic field oscillating greater than about 1 GHz to cause the spin polarization of the light signal may be generated, where the light signal being retro-reflective imaged onto a transparent and/or shiny object so as to provide for determining presence of the transparent and/or shiny object.

16 Claims, 13 Drawing Sheets

(56) References Cited

U.S. PATENT DOCUMENTS

| | | |
|---|---|---|
| 8,766,341 B2 | 7/2014 | Han et al. |
| 9,000,433 B2 | 4/2015 | Wunderlich et al. |
| 2002/0084406 A1 | 7/2002 | Thawley et al. |
| 2009/0141409 A1 | 6/2009 | Santos et al. |

OTHER PUBLICATIONS

Holub, M., et al; "Topical Review; Spin-polarized light-emitting diodes and lasers", Journal of Physics D: Applied Physics, Institute of Physics Publishing Ltd., GB, vol. 40, No. 11, Jun. 7, 2007 (Jun. 7, 2007), pp. R179-R203.

European Search Report corresponding to European Application No. EP17 18 3871, dated Dec. 15, 2017.

* cited by examiner

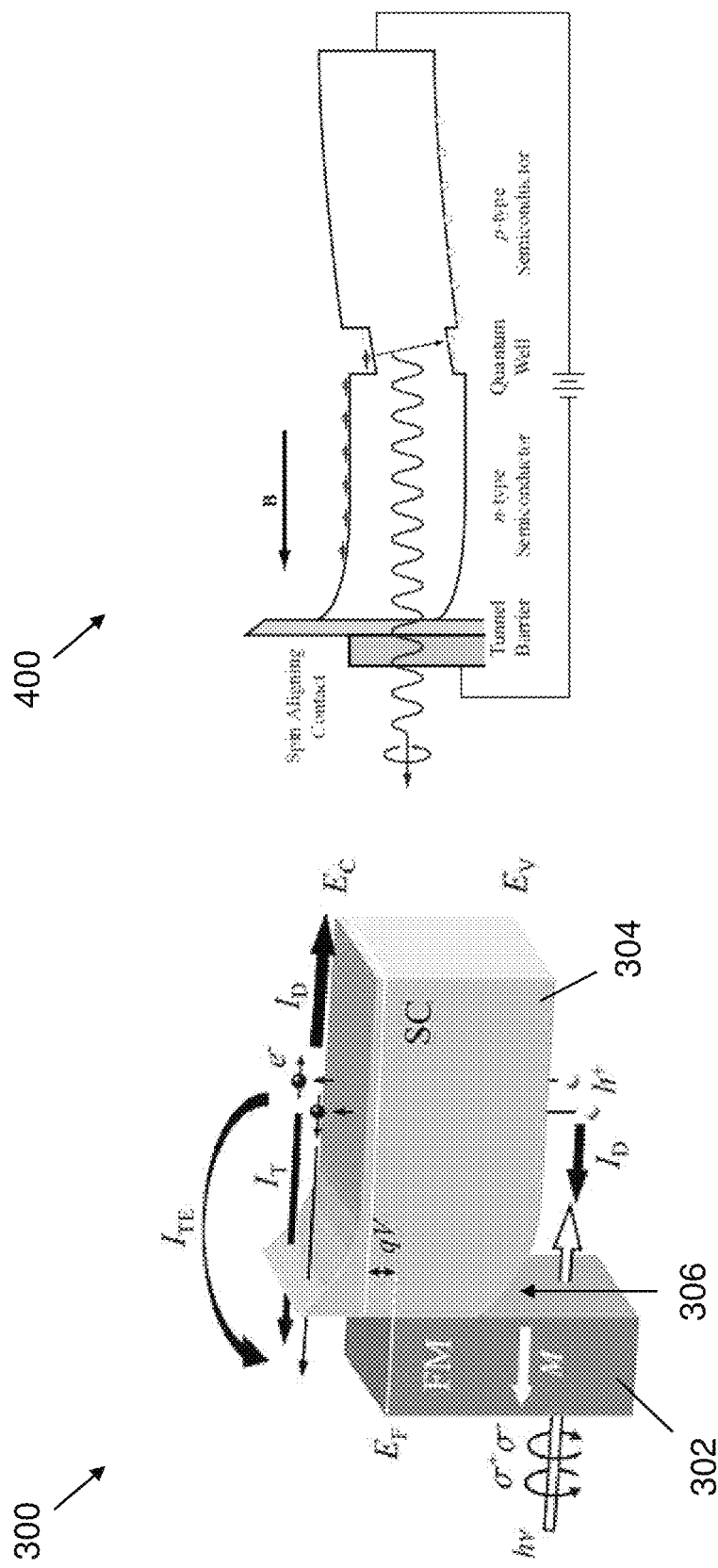

TRANSPARENT AND/OR SHINY OBJECT DETECTION WITH SPIN-MODULATED LIGHT

RELATED APPLICATIONS

This application claims priority to U.S. Provisional Application Ser. No. 62/368,812 filed on Jul. 29, 2016; the contents of which are hereby incorporated herein by reference in their entirety.

BACKGROUND

Optoelectronic devices are used for a variety of different industrial, military, and consumer purposes. Typical optoelectronic devices include an emitter, such as a light emitting diode (LED), and a receiver, such as a photodiode. In operation, an electromagnetic signal (e.g., light beam) is generated by the LED and directly or indirectly received by the photodiode. In practice, a number of configurations may be used for detecting items, including a through-beam configuration, retro-reflective configuration, and proximity-sensing configuration. The through-beam configuration includes an emitter and receiver pair, where the emitter directly illuminates the receiver with an electromagnetic signal. When an item breaks a line-of-sight between an emitter and receiver, the electromagnetic beam is not sensed by the receiver, and detection of the item is made. A retro-reflective configuration is configured with an emitter and receiver typically positioned in a single housing, and where the emitter illuminates a reflector, such as a mirror, that reflects an incident electromagnetic signal onto the receiver. Responsive to the receiver receiving the reflected electromagnetic signal, a determination is made as to whether a change to the reflected electromagnetic signal occurred or whether the electromagnetic signal is blocked completely. A proximity-sensing configuration has an emitter and receiver typically in a single housing, and the emitter outputs an electromagnetic signal onto items as the items enter into a path of the electromagnetic signal. The receiver senses a reflected electromagnetic signal from the item, as opposed to a reflector as with the retro-reflective configuration. The receive signal may be produced at a magnitude commensurate with amplitude or intensity of the reflected electromagnetic signal.

In operation, the receiver (e.g., photodiode) generates a receive signal indicative of receiving an incident electromagnetic signal on the photodiode. Examples of systems that use optoelectronic devices as described above include manufacturing systems that sense existence (through-beam configuration) and integrity (retro-reflective configuration) of a product, automatic garage doors (through-beam configuration) that sense an obstruction of a garage door while closing, robotics that detect objects (proximity configuration) to be grasped, and many other configurations and uses.

One particular sensing task that is difficult for optoelectronic sensing systems to perform includes sensing transparent and/or shiny objects. Such transparent and/or shiny objects include, but are not limited to, clear plastic products (e.g., beverage glass or plastic bottles), products package with clear plastic (e.g., medicines, foods, an other consumer goods), and so forth. For sensing transparent and/or shiny objects, retro-reflective sensing may be used as the reflection of an altered electromagnetic signal is indicative of the transparent and/or shiny objects being positioned between an emitter/receiver pair and reflector, as understood in the art.

Where optoelectronic systems are used to sense transparent and/or shiny objects, polarized electromagnetic or optoelectronic signals may be used. Polarized electromagnetic signals are produced by causing a transverse electric field to be aligned in one direction as opposed to being random or scattered, as understood in the art. An optoelectronic receiving device may be aligned to receive the electromagnetic signal with the polarization filter positioned in front of the electromagnetic receiving device so that if the filter allows the polarized electromagnetic signal to pass with a first, high signal strength, then a determination may be made that the electromagnetic signal has not been altered. Otherwise, if the received electromagnetic signal is received at a second, lower signal strength, then it is determined that an object, in this case a transparent and/or shiny object, is detected due to the polarized electromagnetic signal being rotated such that the filter causes the lower signal of the electromagnetic signal to be sensed by the optoelectronic device.

A variety of optoelectronics system configurations have been used by conventional systems, including configurations with multiple optoelectronic emitters that turn on and off to utilize distinct polarization, multiple polarized filters, rotating polarized filters, and so forth. These optoelectronic systems, however, are expensive, complex, and use additional space. Traditional detectors are generally calibrated with a single polarization configuration, so these detectors are to be adapted manually to the type of object being detected. Such manual calibration is time consuming and expensive.

In the case of using multiple polarizing filters, one at the transmitter and one at the receiver rotated 90° from one another, shiny and/or transparent objects may be a problem. In other configurations, the filters and/or other components may be electromechanically rotated so as to provide for different polarizations of the electromagnetic signal. However, electromechanical rotation of physical devices may be slow. The use of microelectronic machines (MEMS) devices may be faster, but cost and space issues still exist. Accordingly, a system that addresses the above-describe shortcomings for optoelectronic sensing systems is needed.

SUMMARY

A combination of optoelectronic devices that include spintronics technology and a magnetic layer in one or more optoelectronic transmitter and receiver may provide for the ability to perform polarization and modulation of electromagnetic signals very fast without the use of polarization filters. In addition, calibration may be performed electronically and automatically. Such electronic devices may provide for an optoelectronics sensing system that addresses the shortcomings of existing optical electronic systems for sensing transparent and/or shiny objects.

One embodiment of an apparatus for sensing transparent and/or shiny objects may include a spin polarized optoelectronic emitter device configured to generate illumination signals that, in response to a first electrical signal being applied to the spin polarized optoelectronic emitter device, produces a first illumination signal with a first circular polarization. In response to a second electrical signal being applied to the spin polarized optoelectronic emitter, the spin polarized optoelectronic emitter device may be configured to produce a second illumination signal with a second circular polarization. A spin photodiode may be configured to detect the first illumination signal and the second illumination signal reflected from a reflector and via transparent and/or shiny objects. A first electronic circuit may be configured to alternately generate the first and second electrical signals. A second electronic circuit configured to determine whether a transparent and/or shiny object is present by comparing (i) intensity level of the detected reflected illumination signals with (ii) intensity level of a calibration reflected illumination signal, whereas a difference in intensity levels is indicative of a difference between the first and the second circular polarizations.

One embodiment of a method for sensing transparent and/or shiny objects may include producing a first illumination signal with a first circular polarization. A second illumination signal may be produced with a second circular polarization. The first illumination signal and the second illumination signal reflected from a reflector and via transparent and/or shiny objects may be detected. A determination may be made as to whether a transparent and/or shiny object is present by comparing (i) intensity level of the detected reflected illumination signals with (ii) intensity level of a calibration reflected illumination signal, whereas a difference in intensity levels is indicative of a difference between the first and the second circular polarizations.

An embodiment of an imaging system may include a spin LED configured to generate a light signal having a spin polarization. A spin photodiode may also be included, where the spin polarization of the light signal emitted from the device having a spin polarization may be produced by a magnetic field oscillating greater than about 1 GHz.

One embodiment of a method for retro-reflective imaging transparent and/or shiny objects may include generating a light signal having a spin polarization. A magnetic field oscillating greater than about 1 GHz to cause the spin polarization of the light signal may be generated, where the light signal being retro-reflective imaged onto a transparent and/or shiny object so as to provide for determining presence of the transparent and/or shiny object.

One embodiment of an apparatus may include a spin polarized LED emitter configured to emit a circularly polarized light signal. A spin photodiode may be configured to detect reflected light signals. A detection circuit may be in communication with the spin photodiode, and be configured to, after calibration of a reflected circularly polarized light signal with a reflector to generate a reference reflection signal, a reflection signal in the presence of a transparent and/or shiny object may be received. The reflection signal may be compared with the reference reflection signal. A determination that polarization spin of the circularly polarized light signal has changed based on the comparison between the reflection signal and reference reflection signal may be made. Responsive to determining that the polarization spin of the circularly polarized light signal has changed, a determination that the transparent and/or shiny object is present may be made.

One method for imaging transparent and/or shiny objects may include emitting a circularly polarized light signal. Reflected light signals may be detected. After calibrating a reflected circularly polarized light signal with a reflector to generate a reference reflection signal, a reflection signal in the presence of a transparent and/or shiny object may be received. The reflection signal with the reference reflection signal may be compared. A determination that polarization spin of the circularly polarized light signal has changed based on the comparison between the reflection signal and reference reflection signal may be made. Responsive to determining that the polarization spin of the circularly polarized light signal has changed, a determination that the transparent and/or shiny object is present may be made.

BRIEF DESCRIPTION OF THE DRAWINGS

Illustrative embodiments of the present invention are described in detail below with reference to the attached drawing figures, which are incorporated by reference herein and wherein:

FIG. 3 is an illustration of photoexcited charge transport processes in a ferromagnetic layer/semiconductor (FM/SC) Schottky barrier structure at a moderate forward bias;

FIG. 4 is an illustration of a spin-LED band;

DETAILED DESCRIPTION OF THE DRAWINGS

Figure 1:
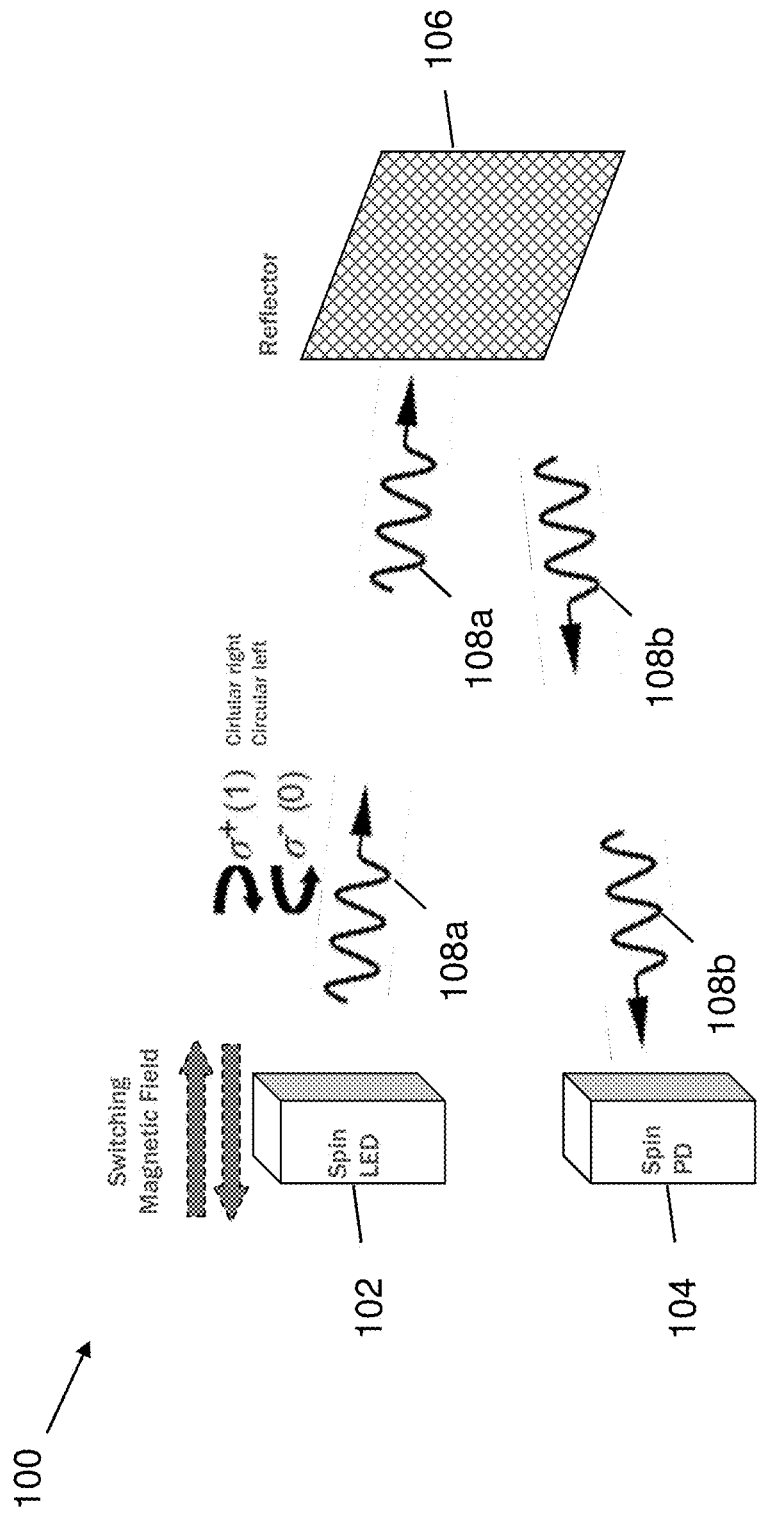
FIG. 1 is an illustration of an illustration of an illustrative optoelectronic apparatus being configured to operate within a retro-reflective arrangement for identifying transparent and/or shiny items.

With regard to FIG. 1, an illustration of an illustrative optoelectronic apparatus 100 being configured to operate within a retro-reflective arrangement for identifying transparent and/or shiny items is shown. As provided, the optoelectronics apparatus 100 may include an emitter 102 configured with spintronics (e.g., spin light-emitting diode) or emitter 102 and receiver 104 configured with spintronics (e.g., spin photodiode). The emitter 102 may be considered a spin polarized optoelectronic emitter device, as spintronics are electronics that provide an intrinsic spin of an electron and associated magnetic moment in addition to a fundamental electronic charge in a solid-state device. Spintronics use both magnetic and electrical fields for causing the spin of the electron and associated magnetic moment, which in the case of generating an electromagnetic signal (e.g., light beam), causes the electromagnetic signal to be polarized, as further described herein. The apparatus 100 may be used to form a retro-reflective sensor or a through beam sensor.

A reflector 106 is positioned and oriented to provide for the retro-reflective arrangement to cause an incident electromagnetic signal (e.g., light beam) 108a generated by the emitter 102 to be reflected as a reflected electromagnetic signal 108b onto the receiver 104. As shown, the incident electromagnetic signal 108a may have a circular-right or circular-left polarization as a result of a magnetic field being applied to a particular layer within the emitter 102, as further described herein.

As previously described, and in accordance with the principles described herein, spin-LEDs and spin-photodiodes may be used to create optoelectronic sensors, especially for retro-reflex or retro-reflective electronics, to realize a modulation of light polarization without moving parts. By eliminating moving parts, less cost, less space, and higher bandwidths of electronic devices for generating and/or receiving polarized electromagnetic signals may be produced.

Retro-reflective sensors may be used to (i) detect transparent objects because transparent objects attenuate, at least a measurable amount, a reflected electromagnetic signal 108b from the reflector, and (ii) distinguish between a reference electromagnetic signal (reflected from the reflector) and a shiny object (like a mirror) that reflects the electromagnetic signal back to the emitter. A mirror inverts the circular polarization of the incident electromagnetic signal, while a reflector can be designed to provide the same circular polarization of the incident electromagnetic signal.

Usually in these applications, polarizing filters and linear polarization are used. However, the receiver generally is limited to amplitude information and a mirror (or shiny object) close to the sensor (e.g., transmitter and receiver in the same housing) may provide such a high reflection signal that may be misidentified as a far reflector signal. Using spin technology, both polarizations may be determined in order to evaluate the total polarization of the received electromagnetic signal, thereby making detection of transparent and/or shiny objects stronger.

Figure 9:
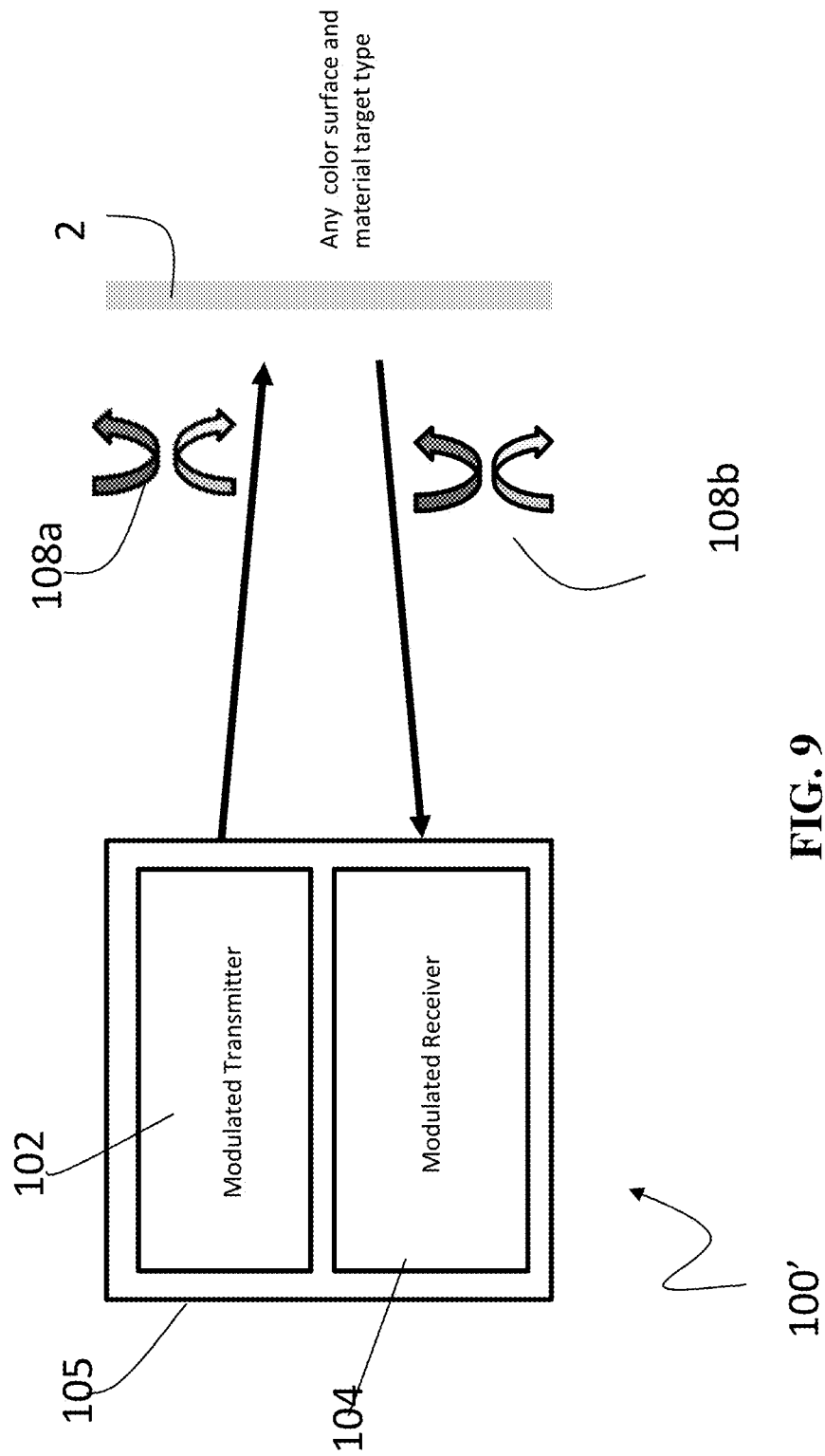
FIG. 9 is an embodiment of a sensor including the apparatus of FIG. 1.

An embodiment of a retro-reflective sensor 100' is given in FIG. 9. The emitter 102 and receiver 104 may be included in the same casing 105. The sensor 100' works in a diffuse mode, that is, the receiver 104 may operate to receive and analyze the diffused electromagnetic signal 108b from an object 2. Object 2 can be any object and the sensor may detect its presence, characteristics, etc. A further embodiment of a retro-reflective sensor 100" is given in FIG. 10. The emitter 102 and receiver 104 may be included in the same casing 105. The sensor 100" works in reflective mode, that is, the sensor 100" may be mechanically and/or electromechanically and/or optically coupled to reflector 3 and receiver 104 becomes aware of the presence of object 2 because the object 2 interrupts or modifies the reception of electromagnetic signal 108b reflected from reflector 3. Object 2 can be any object.

Transparent object detection with spintronic technology may also be used in through-beam sensors (e.g., emitter and receiver in a separate housing without a reflector). In this case, when the signal moves from emitter to receiver through a transparent object, both amplitude and polarization may change, thereby resulting in a larger intensity change. Shiny object detection in this case is intrinsic in the detection principle.

Figure 11:
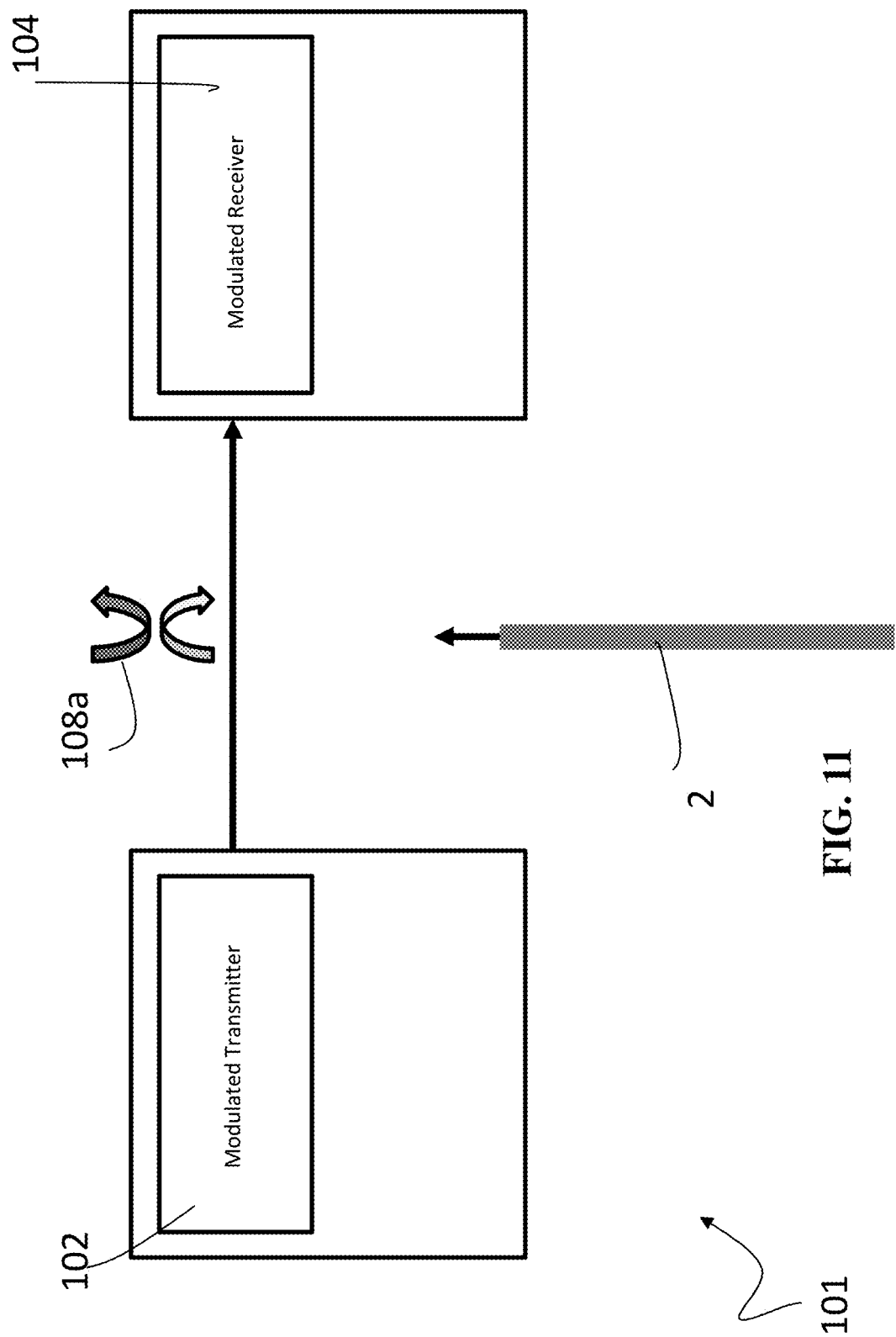
FIG. 11 is a further embodiment of a sensor including the apparatus of FIG. 1.

An embodiment of the through-beam sensor 101 is given in FIG. 11. Emitter 102 and receiver 104 are positioned in two different casings. The emitter 102 and receiver 104 may be electromagnetically in communication with one another during operation. The object 2 interrupts or modifies the reception of the electromagnetic signal 108a.

In operation, modulation of light or electromagnetic signals may be performed by switching magnetization of a magnetic layer inside the emitter 102, in this case by spin-LED, by altering an electrical signal. Light modulation filtering may also be applied to the receiver 104, in this case the spin-photodiode, by switching magnetization of a magnetic layer inside the receiver by altering an electrical signal. The devices may have a ferromagnetic/semiconductor interface (not shown) that selects alignment of spin-polarized electrons. By switching a magnetic field direction, spin-alignment of the filtered electrons may be selected, thereby providing for polarized light.

In an alternative to an internal magnetic layer, the flipping of the magnetization of the emitter 102 and/or receiver 104 may be realized with a switching magnetic field external to the emitter 102 and/or receiver 104. Such external magnetic field switching may be slower and more expensive than the inclusion of a magnetic layer in the optoelectronic device(s). An integrated configuration of optoelectronic devices may be the same or similar to that of Tunnel Magnetoresistance (TMR) memory (MRAM) electronic devices. In the integrated technique, no external magnetic field is utilized, but rather flipping of the magnetization of the emitter 102 and/or receiver 104 is performed through applying an electrical signal to the spin device(s) (i.e., the spin-LED and/or spin-photodiode). This integrated magnetization technique allows high-speed commutation (e.g., higher than about 1 GHz) to produce very fast pulse modulated light signals, which is not possible with a mechanical modulation of the polarization. Other, lower pulse modulation speeds are possible, as well.

In addition to pulse modulation of the emitted electromagnetic signal (amplitude modulation), a modulation of the light polarization may also be utilized. The use of light polarization may provide for the ability to double check the received signal, where both amplitude and polarization modulation can be verified, thereby making detection of transparent and/or shiny items stronger. And, by utilizing amplitude and polarization modulation with a single optoelectronic device, cost is reduced and efficiency is increased.

Figure 7:
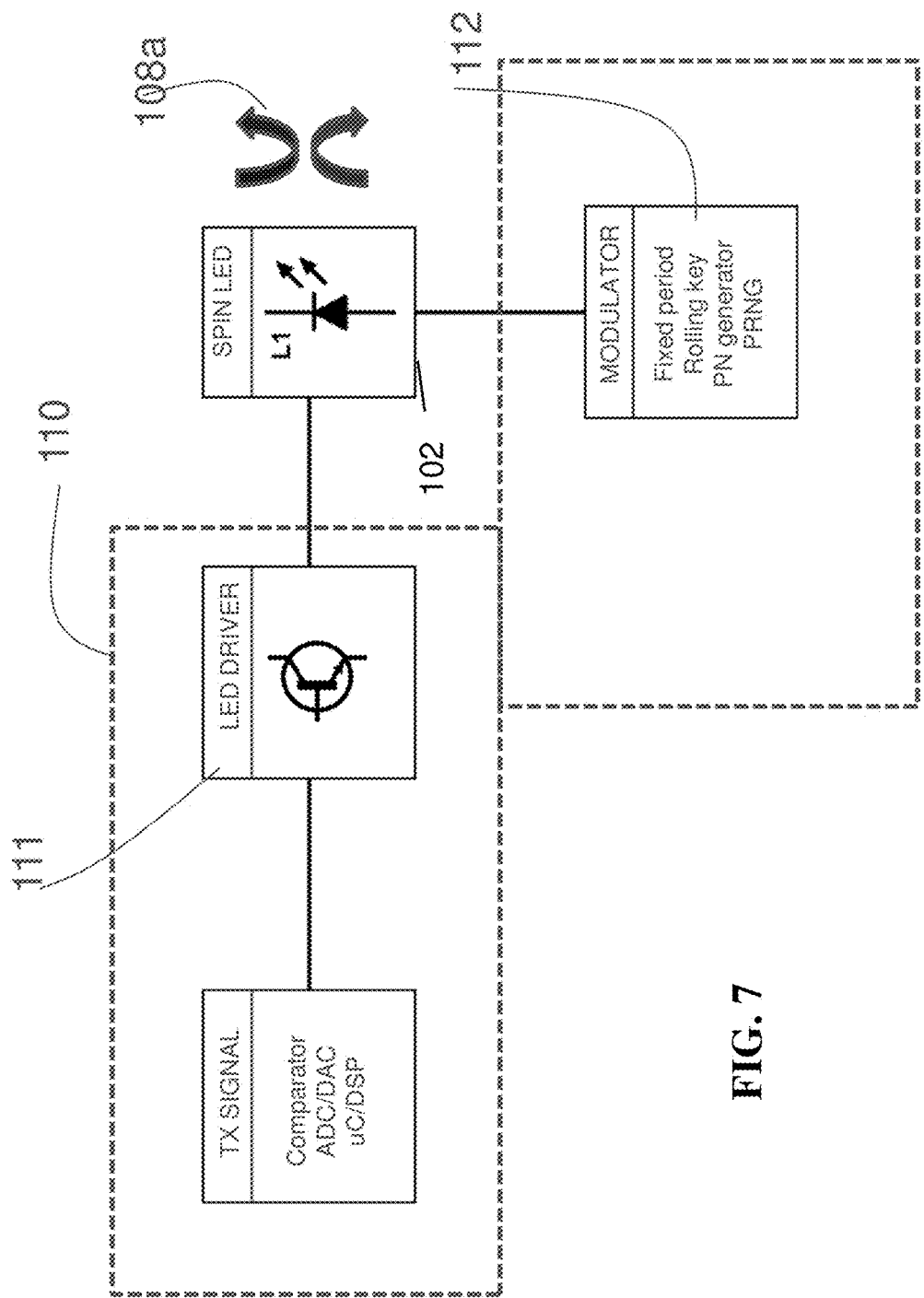
FIG. 7 is an illustration of a portion, in more details, of the apparatus of FIG. 1.

The emitter (spin LED 102) may therefore generate a different illumination signal 108a depending on an electrical signal generated by a first circuit 110. An embodiment of the first circuit is shown in FIG. 7. The first electronic circuit 110 may include an LED driver 111. Further, the first electronic signal may also include a modulator 112. The modulator 112 is used to select the polarization of the emitted illumination signal 108a. The modulator 112 may include produce any kind of modulating signal with a predefined period of modulation or a pseudo-random timing.

On the receive side, the receiver 104, in this case a spin-photodiode, may be utilized to demodulate the reflected electromagnetic signal 108b from the reflector 106. The use of a receiver 104 (e.g., spin-photodiode) may provide for receiving the reflected electromagnetic signal 108b that is a modulated polarized signal by setting the receiver 104 with a particular polarity or dynamically altering the polarity of the receiver 104, thereby providing for filtering of the polarized electromagnetic signals.

Figure 8:
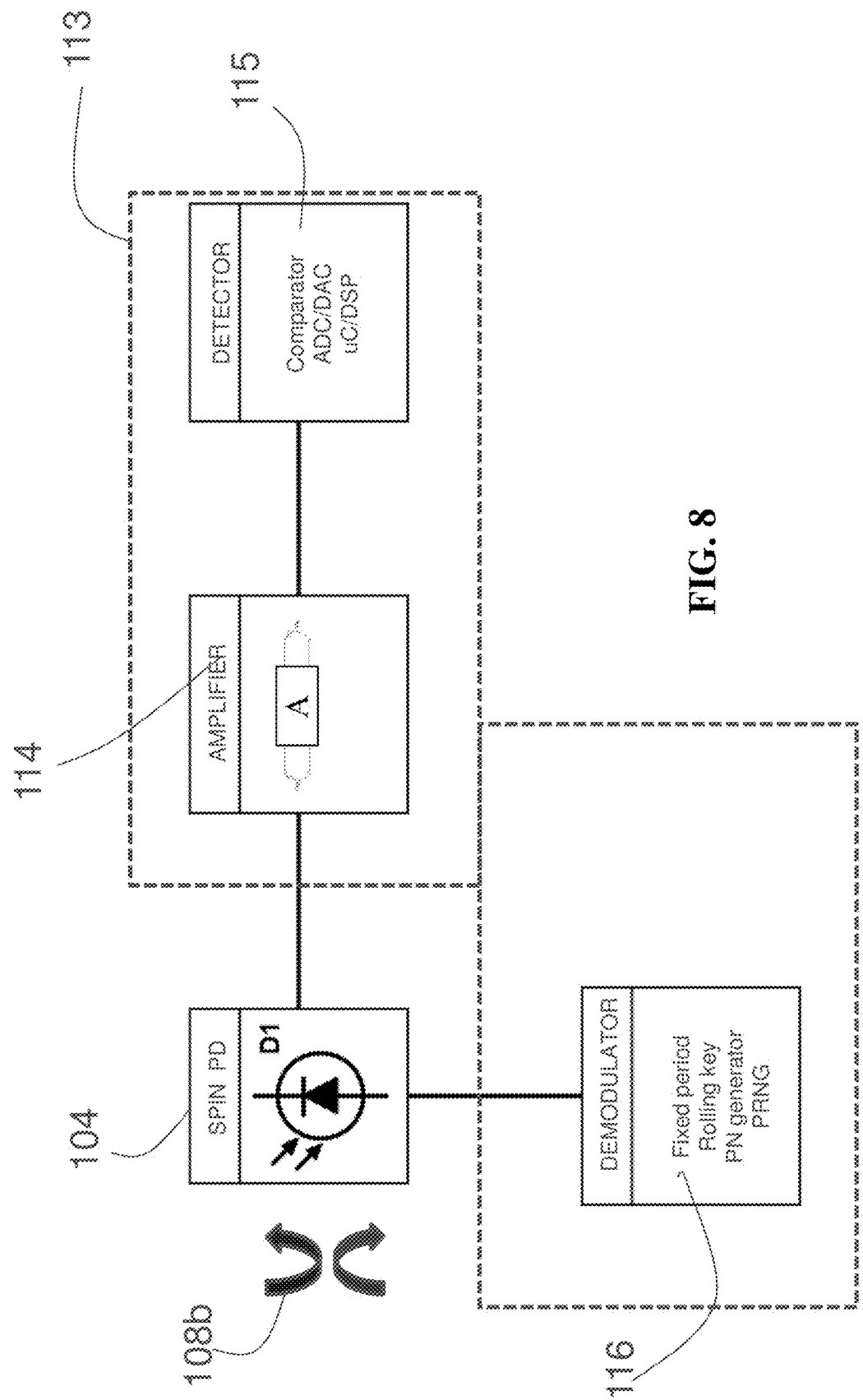
FIG. 8 is an illustration of a further portion, in more details, of the apparatus of FIG. 1.

The receiver 104 may be electrically and/or optically coupled to a second electronic circuit 113, an embodiment of which is depicted in FIG. 8. The second electronic circuit 113 may include an amplifier or amplification stage 114 for amplifying a photodiode current emitted by the receiver 104 and also a detector or elaboration stage 115 where the elaboration is performed, that is, where, for example, a comparison is made between the intensity level of the detected reflected illumination signals 108b and the intensity level of a calibration reflected illumination signal that may be pre-established during calibration of the optoelectronics apparatus 100 for use in determining whether a transparent and/or shiny object is present.

The amplification stage 114 may comprise a transimpedence amplifier. The elaboration stage 115 may include an analog-to-digital converter, or a comparator, or a combination thereof, or any other kind of elaboration unit to analyze the signal coming from the amplification stage 114.

The second electronic circuit 113 may also include a demodulator 116. This demodulator 116 may provide reverse functionality as the modulator 112 used in the first electronic circuit 110. The demodulator 116 acts on the spin-photodiode 104 in order to change sensitivity to light polarization.

Figure 2:
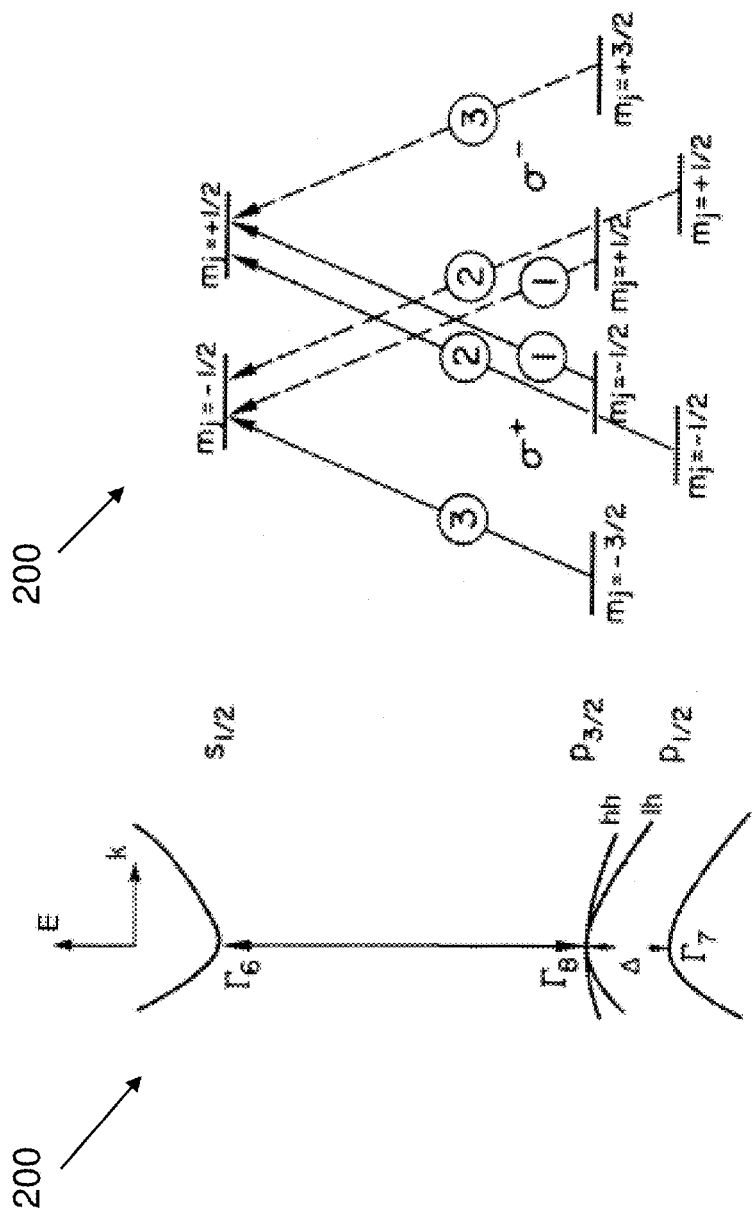
FIG. 2 is an illustration of illustrative energy bands at the center of a Brillouin zone showing band gap energy Eg and spin-orbit splitting of the valance band Δ.

With regard to FIG. 2, an illustration of illustrative energy bands 200 at the center of a Brillouin zone showing band gap energy Eg and spin-orbit splitting of the valence band A is shown. By further way of background, it has been discovered that spin-LEDs and spin-photodiodes are devices that are sensitive to electromagnetic signal (light) polarization. In particular, spin-LEDs use polarized electrons to emit circularly-polarized light, while spin photodiodes provide a current signal depending on the helicity of the incident light. Spin polarization technology is based on the spin polarized photoemisson (spin-LEDs) and spin Polarized Photo-Luminescence (spin photodiodes).

More particularly, spin-LEDs emit circularly-polarized photons depending on spin-alignment of electrons involved in the electron-hole recombination. Spin-up and spin-down electrons, respectively, generate circularly-right and circularly-left polarized light.

Spin-photodiodes show a current-dependence on the heliticity of the incident light. Spin photodiodes have a broken symmetry in the valence band. When photons are absorbed, spin photodiodes generate a current of spin-aligned electrons in the conduction band. The maximum current variation ΔI is detected with circularly-polarized photons.

The principle of a polarized electron source relies on photoexcitation of spin-polarized electrons in a solid substrate. The possibility to optically generate a population of spin polarized electrons in a conduction band of a solid substrate may be utilized in a wide number of optical systems. This generation of spin polarized electrons is the consequence of the fact that the only two experimental requirements are the excitation of the electrons with circularly-polarized light of convenient energy and the choice of at least one state of a band, involved in the transition, where the orbital degeneration is removed due to Spin Orbit Interaction (SOI), magnetic Zeeman effect, and/or stressed crystal structures. It should be understood that alternative ways to break orbital degeneration may be utilized, as well.

The origin of spin polarization can be understood with reference to FIG. 2. As depicted are energy bands 200 at the center of the Brillouin zone showing the band gap energy Eg and the spin-orbit splitting of the valence band Δ. The allowed transitions between $m_j$ sublevels for circularly polarized light, positive helicity σ⁺ (solid lines, $\Delta m_j=1$) and negative helicity σ⁻ (dashed lines, $\Delta m_j=-1$), with relative transition probabilities is given by the circled numbers. These transitions follow the quantum mechanics selection rules for photons absorption.

The polarization is defined as $P=(N\uparrow-N\downarrow)/(N\uparrow+N\downarrow)$, where $N\uparrow$ ($N\downarrow$) are the number of electrons with spins parallel (anti-parallel) to a quantization direction. In FIG. 2, an example of a net polarization of photoexcited electrons from a valence band to conduction band is due to the Spin-Orbit interaction, which breaks the symmetry of the system. The valence band degeneration can also be broken with stressed crystals and quantum wells (or multiple quantum wells).

With regard to FIG. 3, an illustration of photoexcited charge transport processes 300 in a ferromagnetic layer 302/semiconductor layer 304 (FM/SC) Schottky barrier structure at a moderate forward bias is shown. From a technological point-of-view, spin polarization devices may be produced similar to traditional photodiodes and LEDs with a ferromagnetic layer added to produce or filter electron-spins. In spin-photodiodes, the photoexcited electrons passing from the semiconductor layer 304 into the ferromagnetic layer 302 have different transmission probabilities at a SC/FM interface 306 depending on spin orientation with respect to magnetization of the FM layer 302. In this way, a spin imbalance of the electron current can be detected and measured as a modulation of the photocurrent. Spin-LEDs may use the same SC/FM interface 306 to filter the spin orientation of the injected charges in a conduction band. Photon generation is a result of radiative electron-hole recombination in the active layer of the device. This transition may occur between the spin-aligned electron in the conduction band and one of several available valence bands.

With regard to FIG. 4, an illustration of a spin-LED band 400 is shown. As previously described, spintronics technology may be used to produce optoelectronic sensors, especially retro-reflective optoelectronic sensors, (i) to detect a transparent and/or shiny object without independent polarizing filters because spin photodiodes provide information also on the polarization of the incident light, and (ii) to realize a modulation of the light polarization without moving mechanical parts as the modulation of the light polarization may be performed by switching the magnetic orientation of the ferromagnetic layer to produce a spin filter.

The use of the retro-reflective optoelectronic sensors described herein may support numerous applications. As an example, and in addition to the application of detecting transparent and/or shiny objects, the retro-reflective optoelectronic sensors with modulated polarization may provide for identifying different transparent and/or shiny substrates based on polarization responses of the different substrates. That is, different substrates may respond with a different response signature to the electromagnetic signals with different polarizations, including different high-frequency (e.g., greater than about 1 GHz) light polarization modulation that may be produced utilizing the internal magnetic layer of the spin optoelectronic devices described in FIG. 1.

Figure 10:
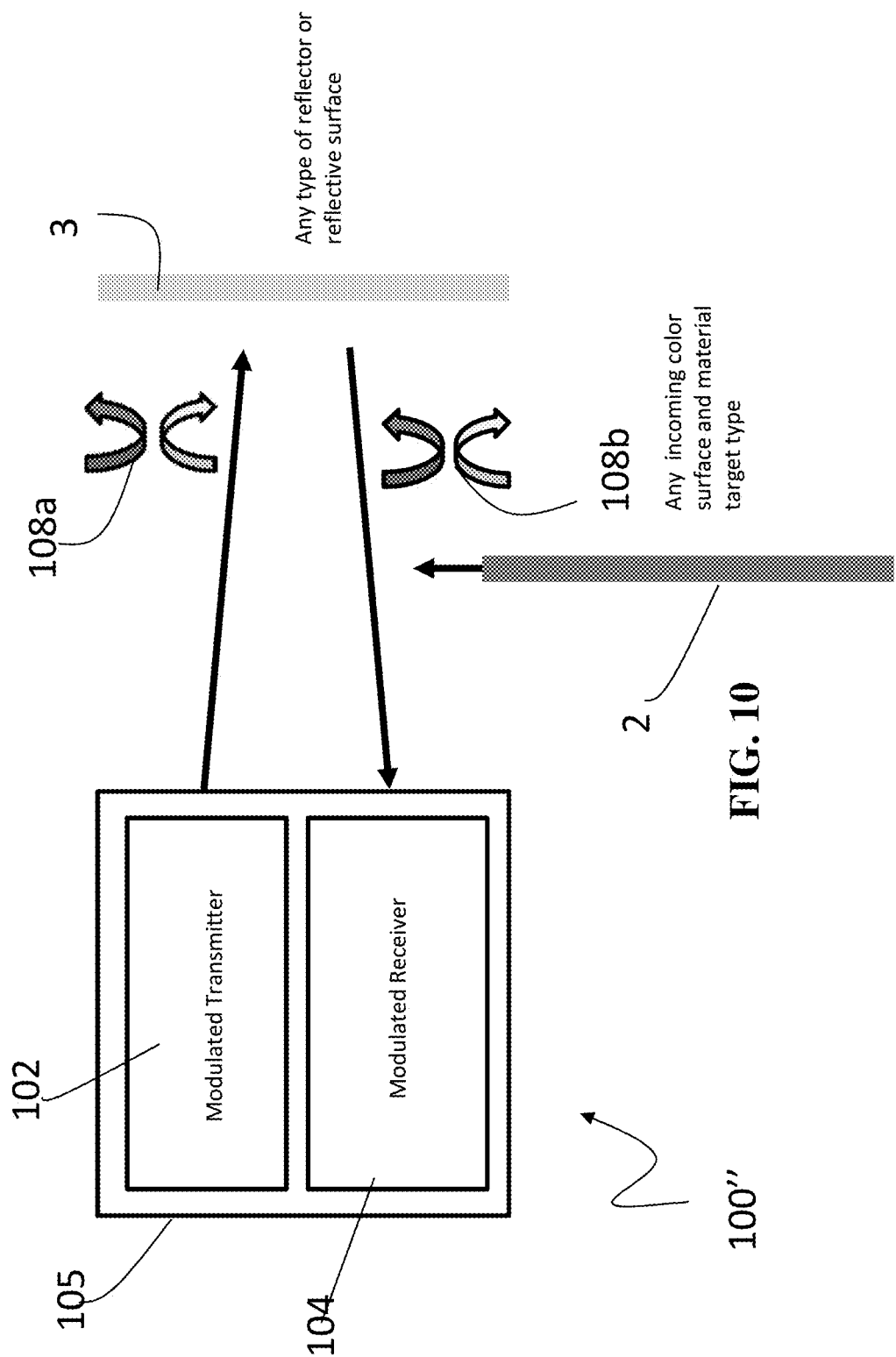
FIG. 10 is a further embodiment of a sensor including the apparatus of FIG. 1.
Figure 12:
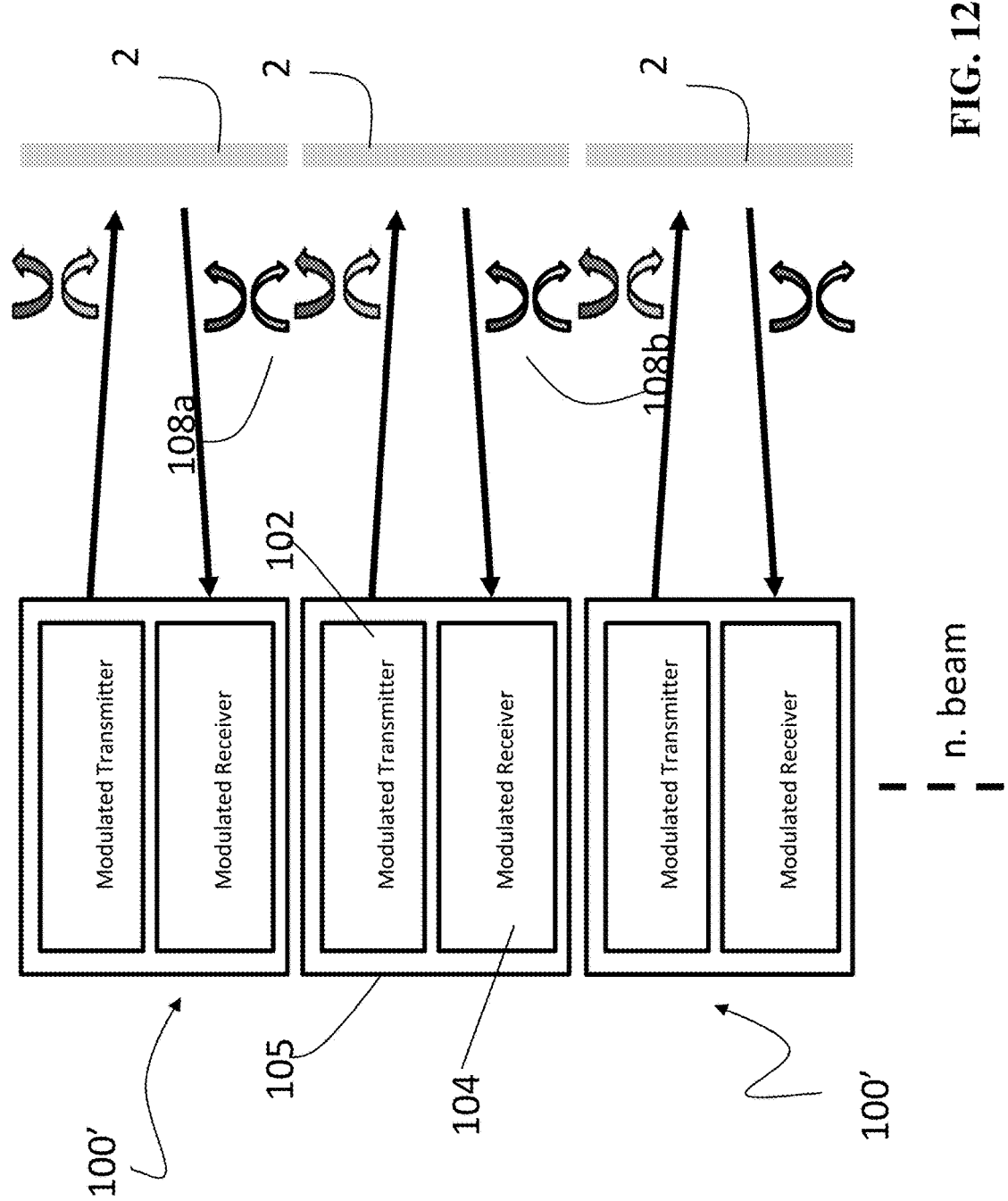
FIG. 12 is an embodiment of a sensor including a plurality of apparatuses of FIG. 1.
Figure 13:
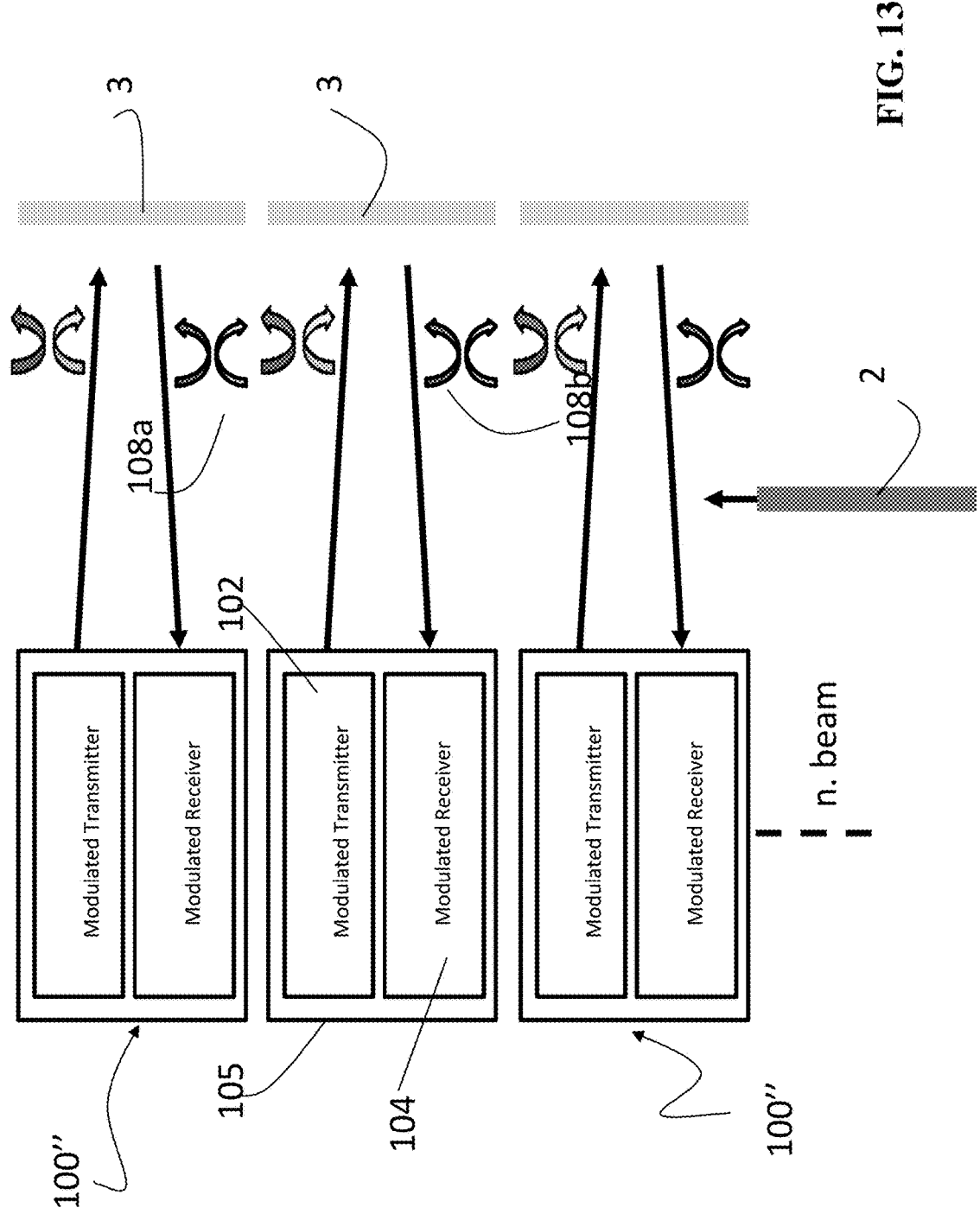
FIG. 13 is a further embodiment of a sensor including a plurality of apparatuses of FIG. 1.
Figure 14:
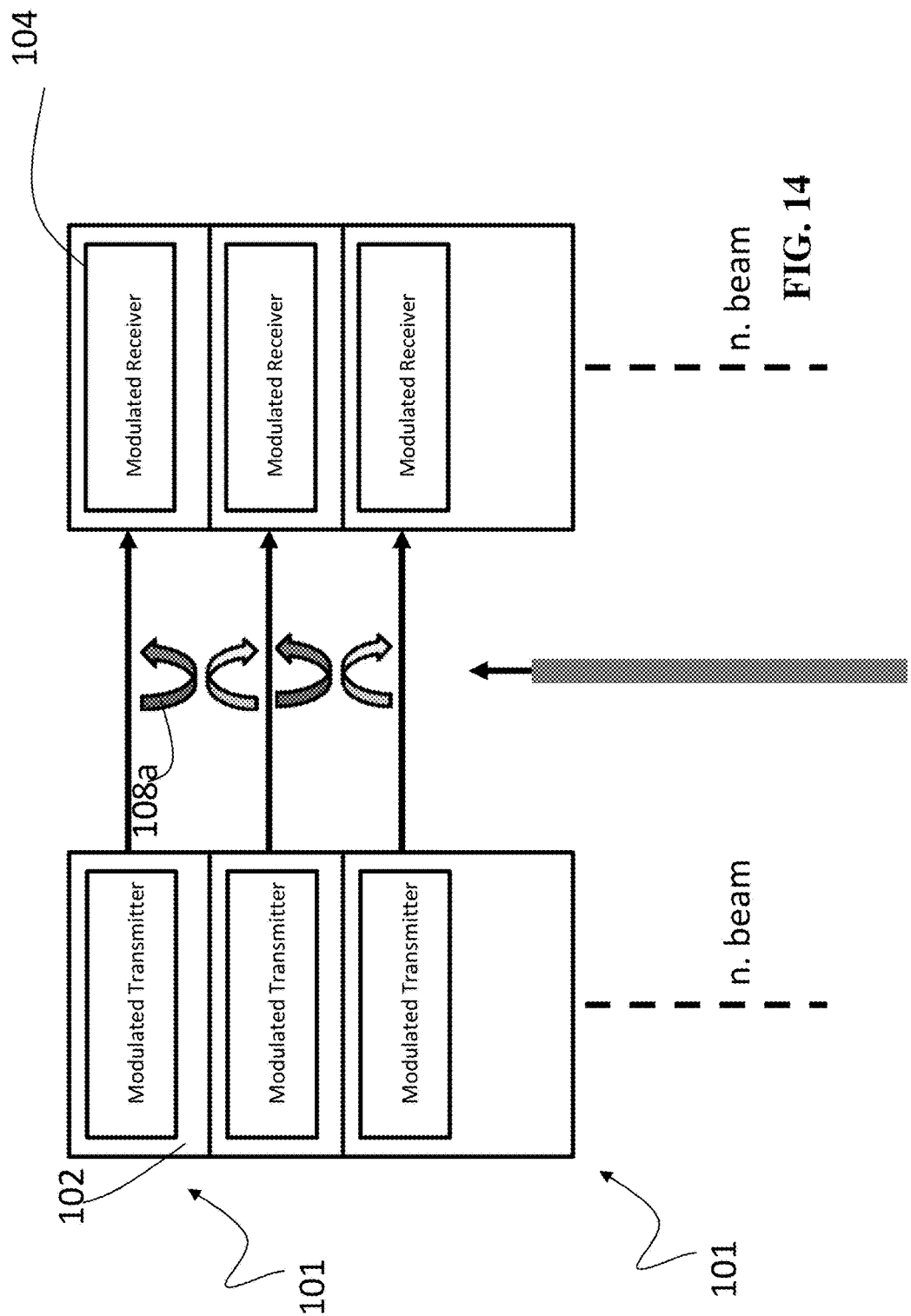
FIG. 14 is a further embodiment of a sensor including a plurality of apparatuses of FIG. 1.

In one embodiment, one spin-LED as described herein may be utilized to produce a retro-reflective or spintronic sensor, as those depicted in FIGS. 9, 10 and 11. In an alternative configuration, multiple spin-LEDs may be utilized, as shown in FIGS. 12, 13 and 14. In FIG. 12, a plurality of sensors 100' of the type shown in FIG. 9 is used to form a light barrier in multi-beam diffuse mode. In FIG. 13, a plurality of sensors 100" of the type shown in FIG. 10 is used to form a light barrier in a multi-beam reflective mode. In FIG. 14, a plurality of sensors 101 of the type shown in FIG. 11 is used to form a light barrier in a multi-beam mode. With one emitter, the emitted light may be tuned as right—(R-) or left—(L-) polarized. With two or more emitters, it is possible to obtain line polarization by properly adjusting relative phase between or among the emitters, such as by using an electronically tunable quarter-wave plate. The spintronic sensor may be added to an existing automatic identification (Auto ID) system by analyzing how a known substrate or material reflects a predetermined type of polarized light so that a known type of material may be automatically identified or determined relative to other substrates.

Such automatic identification may be useful in a number of applications, including a first application that includes Direct Part Marking applications, where a type of substrate may drive use of a type of illumination (color/direction) when creating a marking. A second application may include laser marking, where different marking techniques may be used based on the material reflectivity. A third application may include reading barcodes on reflective surfaces, such as phone screens, where a polarization reflectivity scan may be used to tune illumination, decide what kind of reflective surface is currently under view, and tune the illumination/exposure parameters of a barcode reading camera accordingly. In each of these applications, the addition of a spintronic emitter/receiver to an existing DPM reader camera, barcode reader camera, or laser marking system, as a surface analysis sensor, may bring advantages in better real time response of the system to changing material reflectivity.

Figure 5:
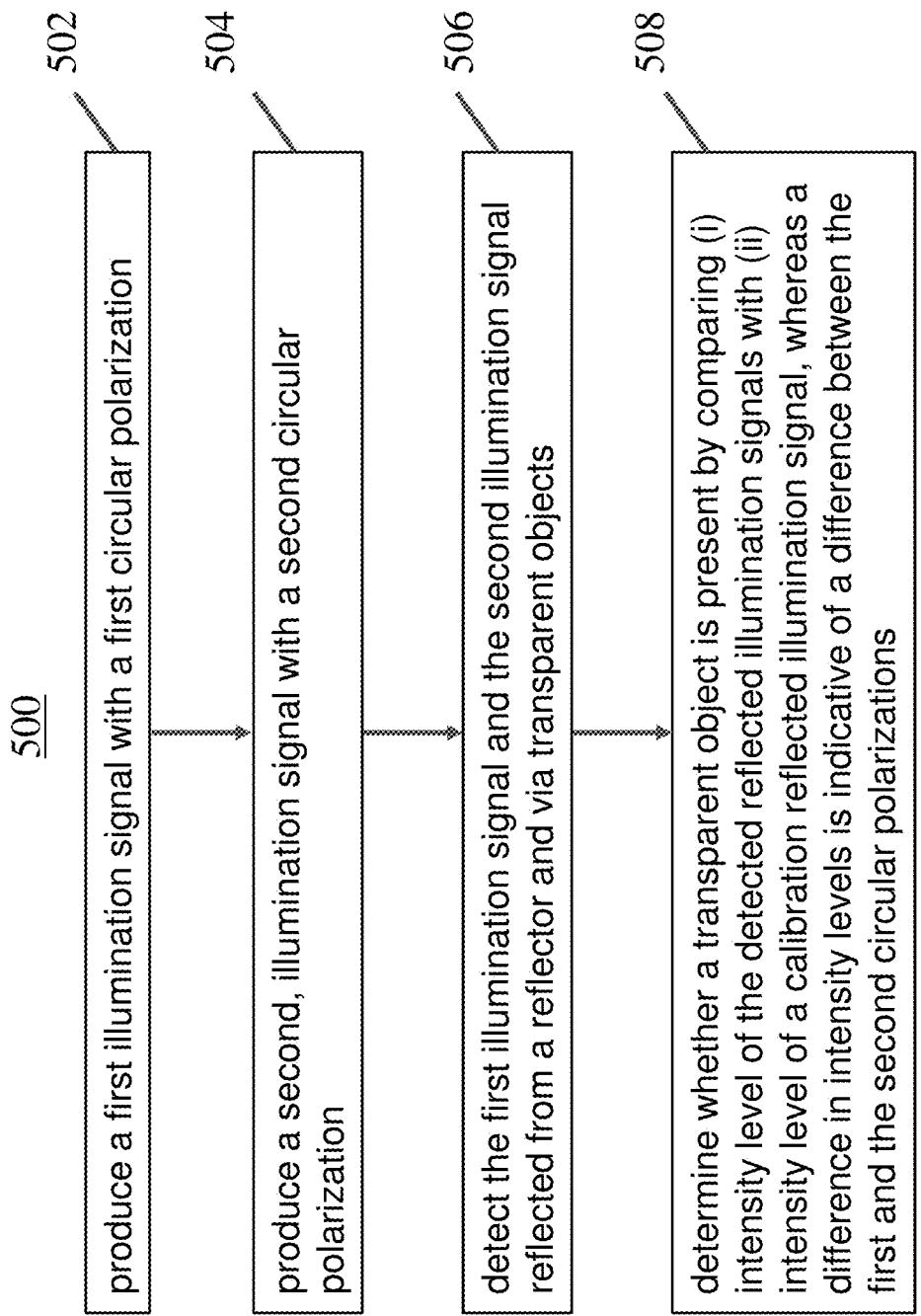
FIG. 5 is a flow diagram of an illustrative process for sensing an object.

With regard to FIG. 5, a flow diagram of an illustrative process 500 for sensing a transparent and/or shiny object is shown. A first illumination signal with a first circular polarization may be produced at step 502. A second, illumination signal with a second circular polarization may be produced at step 504. At step 506, the first illumination signal and the second illumination signal reflected from a reflector and via transparent and/or shiny objects may be detected. At step 508, a determination may be made as to whether a transparent and/or shiny object is present by comparing (i) intensity level of the detected reflected illumination signals with (ii) intensity level of a calibration reflected illumination signal, whereas a difference in intensity levels is indicative of a difference between the first and the second circular polarizations.

Figure 6:
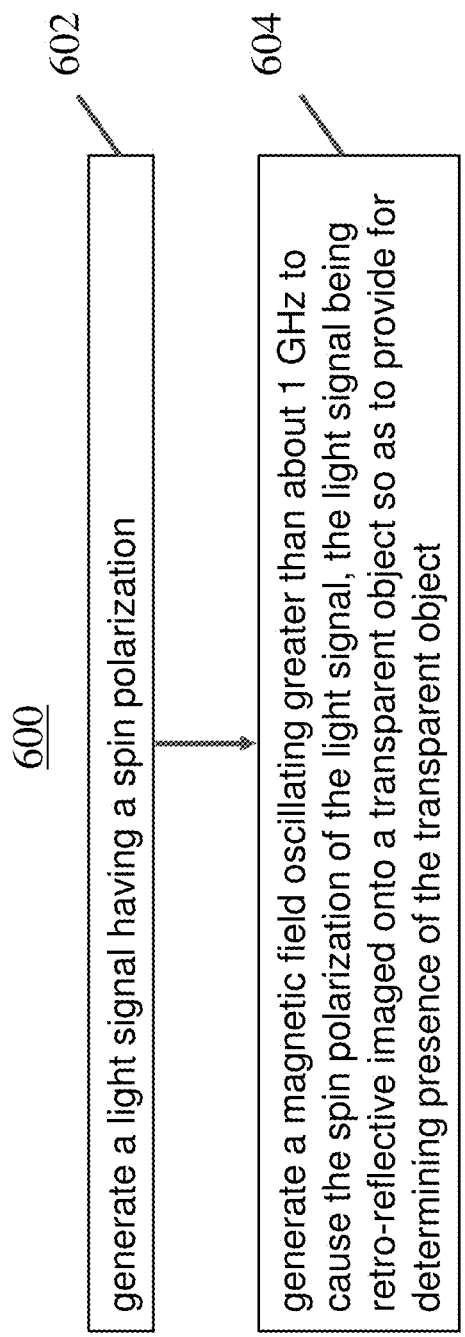
FIG. 6 is a flow diagram of a method for retro-reflective imaging transparent objects.

With regard to FIG. 6, a flow diagram of a method 600 for retro-reflective imaging transparent and/or shiny objects is shown. The process 600 may start at step 602, where a light signal having a spin polarization may be generated. At step 602, a magnetic field oscillating greater than about 1 GHz to cause the spin polarization of the light signal may be generated. The light signal may be retro-reflectively imaged onto a transparent and/or shiny object so as to provide for determining presence of the transparent and/or shiny object.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the principles of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed:

1. An apparatus for sensing transparent and/or shiny objects, comprising:
    a spin polarized optoelectronic emitter device configured to generate illumination signals that, in response to a first electrical signal being applied to said spin polarized optoelectronic emitter device, produces a first illumination signal with a first circular polarization, and in response to a second electrical signal being applied to said spin polarized optoelectronic emitter, produces a second illumination signal with a second circular polarization;
    a spin photodiode configured to detect the first illumination signal and the second illumination signal reflected from a reflector and via transparent and/or shiny objects;
    a first electronic circuit configured to alternately generate the first and second electrical signals; and
    a second electronic circuit configured to determine whether a transparent and/or shiny object is present by comparing (i) intensity level of the detected reflected illumination signals with (ii) intensity level of a calibration reflected illumination signal, whereas a difference in intensity levels is indicative of a difference between the first and the second circular polarizations.

2. The apparatus according to claim 1, wherein when said first electronic circuit generates the first electrical signal, said second electronic circuit determines whether the transparent and/or shiny object is present, and wherein when said first electronic circuit generates the second electrical signal, said second electronic circuit determines whether the transparent and/or shiny object is present.

3. The apparatus according to claim 2, wherein said first electronic circuit is configured to generate the first and second electrical signal multiple times per second to cause the spin polarized optoelectronic emitter device to produce a modulated circularly polarized illumination signal by switching between a left and a right circular polarization, and wherein said second electronic circuit is configured to determine whether the transparent and/or shiny object is present during each of the left and right circular polarization illumination signals.

4. The apparatus according to claim 3, wherein the first electronic device is configured to alternate generating the first and second electrical signals at a frequency greater than about 1 GHz, and wherein said second electronic circuit is configured to determine whether the transparent and/or shiny object is present during each left and right circular polarization illumination signals.

5. The apparatus according to claim 1, wherein said first electronic circuit is configured to generate the first and second electrical signals to cause the spin polarized optoelectronic emitter device to produce a modulated first illumination signal with a first circular polarization and to cause the spin polarized optoelectronic emitter device to produce a modulated second illumination signal with a second circular polarization.

6. The apparatus according to claim 1, wherein the first circular polarization is a left circular polarization, and wherein the second circular polarization is a right circular polarization.

7. The apparatus according to claim 1, wherein said second electronic circuit is further configured to determine whether the transparent and/or shiny object is present by comparing polarization of the first and second circular polarizations relative to the calibration reflected illumination signal.

8. The apparatus according to claim 1, wherein said second electronic circuit is further configured to determine substrate type of the transparent and/or shiny object.

9. A method for sensing transparent and/or shiny objects, comprising:
producing a first illumination signal with a first circular polarization;
producing a second illumination signal with a second circular polarization;
detecting the first illumination signal and the second illumination signal reflected from a reflector and via transparent and/or shiny objects; and
determining whether a transparent and/or shiny object is present by comparing (i) intensity level of the detected reflected illumination signals with (ii) intensity level of a calibration reflected illumination signal, whereas a difference in intensity levels is indicative of a difference between the first and the second circular polarizations.

10. The method according to claim 9, further comprising:
determining whether the transparent and/or shiny object is present when producing the first illumination signal; and
determining whether the transparent and/or shiny object is present when producing the second illumination signal.

11. The method according to claim 10, wherein producing the first and second illumination signals includes generating electrical signals multiple times per second to a modulated circularly polarized illumination signal to be produced by switching between a left and a right circular polarization, and further comprising determining whether the transparent and/or shiny object is present during each of the left and right circular polarization illumination signals.

12. The method according to claim 11, wherein generating the first and second electrical signals includes alternate generating the first and second electrical signals at a frequency greater than about 1 GHz, and determining whether the transparent and/or shiny object is present during each left and right circular polarization illumination signals.

13. The method according to claim 9, further comprising:
producing a modulated first illumination signal with a first circular polarization; and
producing a modulated second illumination signal with a second circular polarization.

14. The method according to claim 9, wherein producing a first circular polarization includes producing a first circular polarization as a left circular polarization, and wherein producing a second circular polarization includes producing a second circular polarization as a right circular polarization.

15. The method according to claim 9, further comprising determining whether the transparent and/or shiny object is present by comparing polarization of the first and second circular polarizations relative to a calibration reflected illumination signal.

16. The method according to claim 9, further comprising determining substrate type of the transparent and/or shiny object.

* * * * *